United States Patent [19]

Teuscher

[11] 3,943,108

[45] Mar. 9, 1976

[54] PHOTOCONDUCTIVE COMPOSITION OF AN ALDEHYDE CONDENSATE

[75] Inventor: Leon A. Teuscher, Webster, N.Y.

[73] Assignee: Xerox Corporation, Stamford, Conn.

[22] Filed: Sept. 27, 1974

[21] Appl. No.: 509,771

[52] U.S. Cl............ 260/73 R; 96/1.5; 204/159.21; 260/64; 260/67 A; 260/67.5; 260/823; 260/874; 427/14
[51] Int. Cl.$^2$.................C08F 257/02; C08L 25/06; G03C 1/00
[58] Field of Search......... 260/67 A, 67.5, 64, 73 R, 260/823, 874; 204/159.21

[56] References Cited
UNITED STATES PATENTS

| | | | |
|---|---|---|---|
| 2,706,725 | 4/1955 | Unruh et al............ | 260/64 |
| 3,554,746 | 1/1971 | Merrill............... | 260/64 X |
| 3,655,378 | 4/1972 | Contois et al......... | 260/67 A X |
| 3,740,218 | 6/1973 | Contois et al......... | 260/67 A X |
| 3,791,824 | 2/1974 | Bauer et al........... | 260/67 R X |

Primary Examiner—Lucille M. Phynes
Attorney, Agent, or Firm—James J. Ralabate; James P. O'Sullivan; John H. Faro

[57] ABSTRACT

Polymeric photoconductive composition having recurring structural units of the formula:

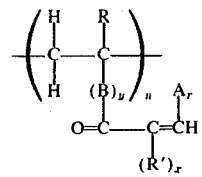

wherein
R is hydrogen or alkyl of 1–4 carbon atoms;
R' is alkyl of 1–4 carbon atoms, cycloalkyl, phenyl, or alkyl substituted phenyl;
B is phenylene or a diradical of a fused aromatic nucleus having up to four benzene rings;
$A_r$ is selected from the group consisting of naphthalene, anthracene, pyrene, perylene, julolidine, carbazole, their respective homologues and analogues;
$x$ is 0 or 1;
$y$ is 0 or 1; and
$n$ is at least 2.

The above polymeric compositions are suitable for use as charge transport matrices for photogenerator materials or can themselves be complexed with an appropriate activator and thus, form a charge transfer complex which is itself capable of photoresponse within the visible region of the electromagnetic spectrum.

9 Claims, No Drawings

3,943,108

PHOTOCONDUCTIVE COMPOSITION OF AN ALDEHYDE CONDENSATE

BACKGROUND OF THE INVENTION

1. Field of the Invention

This invention relates to a composition, articles and methods employing such composition. More specifically, this invention is directed toward polymeric photoconductive compositions suitable for use as charge carrier transport matrices for electrophotographic imaging members. These polymeric compositions can be modified by the incorporation therein of certain activator molecules capable of formation off charge transfer complexes with the bulky planar substituents of the polymer thus rendering the composition photoresponsive within the visible region of the electromagnetic spectrum.

2. Description of the Prior Art

The formation and development of images on the imaging surfaces of photoconductive materials by electrostatic means is well known. The best known of the commercial processes, more commonly known as xerography, involves forming a latent electrostatic image on the imaging surface of an imaging member by first uniformly electrostatically charging the surface of the imaging member in the dark and then exposing this electrostatically charged surface to a light and shadow image. The light struck areas of the imaging layer are thus rendered relatively conductive and the electrostatic charge selectively dissipated in these irradiated areas. After the photoconductor is exposed, the latent electrostatic image on this image bearing surface is rendered visible by development with a finely divided colored electroscopic material, known in the art as "toner". This toner will be principally attracted to those areas on the image bearing surface having a polarity of charge opposite to the polarity of charge on the toner particles and thus form a visible powder image.

The developed image can then be read or permanently affixed to the photoconductor where the imaging layer is not to be reused. This latter practice is usually followed with respect to the binder-type photoconductive films (e.g. zinc oxide/film forming resinous binder) where the photoconductive imaging layer is also an integral part of the finished copy.

In so-called "plain paper" copying systems, the latent image can be developed on the imaging surface of a reusable photoconductor or transferred to another surface, such as a sheet of paper and thereafter developed. When the latent image is developed on the imaging surface of a reusable photoconductor, it is subsequently transferred to another substrate and then permanently affixed thereto. Any one of a variety of well known techniques can be used to permanently affix the toner image to the copy sheet, including overcoating with transparent films and solvent or thermal fusion of the toner particles to the supportive substrate.

In the above plain paper copying system, the materials used in the photoconductive insulating layer should preferably be capable of rapid switching from insulating to conductive to insulating state in order to permit cyclic use of the imaging surface. The failure of a material to return to its relatively insulating state prior to the succeeding charging sequence will result in (an increase in the rate of dark decay) a decrease in the maximum charge acceptance of the photoconductor. This phenomenon, commonly referred to in the art as "fatigue" has in the past been avoided by the selection of photoconductive materials possessing rapid switching capacity. Typical of the materials suitable for use in such a rapidly cycling system include anthracene, sulfur, selenium and mixtures thereof (U.S. Pat. No. 2,297,691); selenium being preferred because of its superior photosensitivity.

In addition to anthracene, other organic photoconductive materials, most notably, poly(N-vinylcarbazole) have been the focus of increasing interest in electrophotography. Most organic photoconductive materials, including the polyvinylcarbazoles, lack the inherent photosensitivity to be competitive with selenium. This need for enhancement of the photoresponse characteristics of these photoconductive materials has thus led to the formulation of these organic materials with other compounds, commonly referred to as "activators". Polyvinylcarbazoles, for example, when sensitized with 2,4,7-trinitro-9-fluorenone exhibit good photoresponse and discharge characteristics and (depending upon the polarity of the surface charge) low dark decay; U.S. Pat. No. 3,484,237. Other organic resins, traditionally considered nonphotoconductive, can also be sensitized with certain activators such as Lewis acids, thus, forming charge transfer complexes which are photoresponsive in the visible band of the electromagnetic spectrum, see for example, U.S. Pat. Nos. 3,408,181 – 190.

Photoconductive polymers, such as poly(N-vinylcarbazole) have also been used in combination with other photoconductive pigments in the formation of electrophotographic imaging members; see U.K. Patent No. 1,343,671 —photoconductive pigments dispersed within a poly(N-vinylcarbazole) matrix and U.K. Patent No. 1,337,228—a photoconductive layer laminated to a layer of poly(N-vinylcarbazole). In both of the above systems, the poly(N-vinylcarbazole) does not participate in photogeneration of charge carriers since the source of illumination in projection of image information onto the imaging member is substantially outside the range of spectral response of vinylcarbazoles. The poly(N-vinylcarbazole) merely acts to transport the charge carriers generated by the other photoconductive materials and, in fact, inadvertent photogeneration of charge carriers by the carbazole matrix can impair the efficiency of transport and result in incomplete discharge of the sensitizing charge in the illuminated areas. Although these composite systems have distinct advantages over the organic photoconductors described previously, (both with regard to electrophotographic speed and mechanical strength), the unsensitized carbazole polymer is moderately chemically unstable. Because of this relative instability, the carbazole will react with oxygen in the air and ozone produced during sensitization and consequently its electronic properties will gradually decline.

Accordingly, the object of the invention is to remove the above as well as related deficiencies in the prior art.

More specifically, it is the principal object of this invention to provide a polymeric composition suitable for use as a charge carrier transport matrix.

It is another object of this invention to provide a polymeric photoconductive composition which is chemically stable to the extent that it does not undergo progressive deterioration of its electronic properties in an electrophotographic environment.

It is yet another object of this invention to provide a polymeric composition which can be sensitized with activators and thus form a charge transfer complex suitable for use in electrophotographic imaging members and methods.

SUMMARY OF THE INVENTION

The above and related objects are achieved by providing a polymeric photoconductive composition having recurring structural units of the formula:

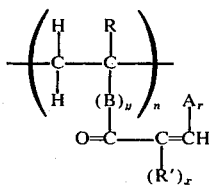

wherein
R is hydrogen or alkyl of 1–4 carbon atoms;
R' is alkyl of 1–4 carbon atoms, cycloalkyl, phenyl, or alkyl substituted phenyl;
B is phenylene or a diradical of a fused aromatic nucleus having up to four benzene rings;
$A_r$ is selected from the group consisting of naphthalene, anthracene, pyrene, perylene, julolidine, carbazole, their respective homologues and analogues;
x is 0 or 1;
y is 0 or 1; and
n is at least 2.

This polymeric composition can be of sufficient molecular weight to independently form self-supporting films or can be copolymerized as a blocked segment with other compatible polymers or engrafted on the backbone of other preformed polymers. In a preferred embodiment of this invention, the value for n of the above composition is in excess of about 40.

DESCRIPTION OF THE INVENTION INCLUDING PREFERRED EMBODIMENTS

The photoconductive compositions of this invention can be prepared by condensation of an aldehyde functional photoresponsive compound with either of the following polymers:

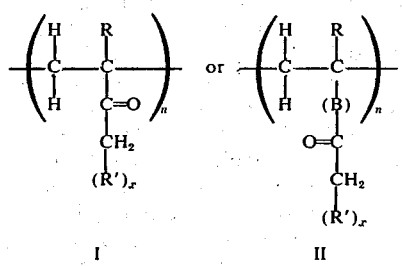

wherein
R, R', B, x and n are as previously defined.

Polymers of the structure of Formula I can be prepared from readily commercially available monomers by well-known addition polymerization techniques, see for example, Chem. Abs. 59-7413(b) and Sorenson and Campbell, "Preparative Methods of Polymer Chemistry", Interscience Publisher Inc., New York (1961), pp. 181–182. Polymers of the structure of Formula II can be prepared by acetylation of the aromatic nucleus of, for example, poly(styrene) with an aliphtic or aromatic acid halide, acid ester or anhydride in the presence of aluminum chloride or other suitable Lewis acid catalyst in accord with conventional Friedel-Crafts synthesis conditions. The condensation of the aldehyde functional photosensitive compound with either of the above polymers can be carried out under standard Crossed Aldol condensation reaction conditions.

Ordinarily the starting materials will determine the ultimate physical properties of the photoresponsive polymeric composition of this invention. For example, where Polymer II (e.g. acetylated poly(styrene) or a substituted acetylated poly(styrene)) is a homopolymer, the photoconductive composition will retain the same basic polymeric structure. In the event that the starting materials is a block copolymer of an acetylated polymer and one or more other polymeric materials, the photoconductive composition will retain this block copolymeric structure. Similarly, where the acetylated polymer is engrafted upon the backbone of another preformed polymeric system, the photoconductive composition will also be graft copolymer in nature.

Depending upon the relative molecular weight of the polymeric photoconductive composition, it can be combined with binders or formed independent of such binders into self-supporting films. The relative thickness of such films can vary within the range of thicknesses traditionally employed for photoconductive insulating layers used in electrophotographic imaging members. For example, such films can be as thin as about 0.1 micron or have a thickness in excess of about 200 microns depending upon the electrophotographic environment and/or whether or not other layers are used in combination therewith in formation of a photoconductive insulating layer.

As indicated previously, such photoconductive layers can form independent self-supporting films or can be coated on any supportive (preferably conductive) substrate. The preferred substrates suitable for use in this invention include any of the substrates commonly employed in preparation of electrophotographic imaging members. Representative of such substates are aluminum, chromium, brass, stainless steel, nickel, their respective alloys, metal coated plastic films (e.g. aluminized Mylar), and semiconductive oxide coated glass plates (NESA glass).

Once having prepared an electrophotographic member from the photoconductive compositions of this invention, such a member can be used in conventional electrophotographic imaging methods and apparatus. In a typical imaging process of this invention, an electrophotographic member having a photoconductive insulating layer prepared from the photoconductive composition of this invention is initially sensitized in the dark by charging with a corona electrode and selectively exposed to image information, thereby forming a latent electrostatic image on the surface of the photoconductive insulating layer. The latent electrostatic image, thus formed, is rendered visible by development with finely divided colored marking materials. The developed image is thereafter transferred from the surface of the photoconductive insulating layer to a receiving sheet. Any untransferred (residual) developer particles remaining on the surface of the photoconductive insulating layer can be removed by wiping with a soft cloth or other suitable cleaning means and the copying cycle repeated.

Where it is desirable to extend the spectral response characteristics of the photoconductive composition beyond that inherently possessed by the composition, activator molecules (e.g. Lewis acids — 2,4,7-trinitro-9-fluorenone) or dyestuff sensitizers can be incorporated within the photoconductive polymer. These materials will provide the polymer with a greater range of spectral response and thereby provide a more panchromatic imaging member.

The Examples which follow further define, describe and illustrate the preparation and use of the polymeric photoconductive compositions of this invention. Apparatus and techniques used in the preparation and evaluation of such compositions are standard or as hereinbefore described. Parts and percentages appearing in such Examples are by weight unless otherwise indicated.

EXAMPLE I

Preparation of julolidine-9-carboxaldehyde

Preliminary to preparation of the photoconductive composition, a reaction vessel comprising a 200 ml. three necked flask which has been fitted with an addition funnel, a mechanical stirring bar, a reflux condenser and a calcium chloride tube attached to the reflux condenser is chilled in an ice bath. Subsequent to lowering the temperature of the flask, about 55.49 grams (0.75 moles) dimethyl formamide is placed in the flask and then about 32.46 grams (0.21 moles) phosphorous oxichloride added thereto with rapid stirring. These two materials form a reddish-orange complex upon their admixture. In a separate container, 36.5 grams (0.21 moles) julolidine is dissolved in dimethyl formamide. The quantity of dimethyl formamide in this second solution is the minimum amount required to dissolve the julolidine. This julolidine solution is now transferred to the addition funnel whereupon it is gradually combined by dropwise addition with the dimethyl formamide/phosphorous oxychloride complex over a period of about 30 minutes. Subsequent to the admixture of the julolidine and the reddish-orange complex, the contents of the flask are heated on a steam bath for about 2 hours, allowed to cool to room temperature, and neutralized to a pH of between 6 to 8 with about 200 ml. of a saturated solution of sodium acetate in water. During this neutralization, the reaction mixture is rapidly stirred with sufficient cooling so as to maintain its temperature at about 20° C. The dimethyl formamide/water layer is extracted three times with 200 ml. portions of benzene and the benzene layer washed 3 times with small portions of water. The benzene layer is then dried over sodium sulfate. As the benzene is allowed to slowly evaporate, a light green solid is formed which is subsequently dissolved in hot cyclohexane. A dark green oily residue which thereafter collects in the bottom of the container, is separated from the cyclohexane, the cyclohexane allowed to cool and the crystals which form therein recovered by filtration; Yield 28.8 grams, m.p. 77°–79° C.

EXAMPLE II

Preparation of the 3-perylencarboxaldehyde

About 22 grams N-methylformanilide is initially dissolved in 40 milliliters o-dichlorobenzene, the vessel containing the above solution partially immersed in a water bath (bath temperature less than 25° C) and 22 grams phosphorous oxychloride introduced into the flask by dropewise addition. About 20 grams of perylene is stirred into the above solution and the resulting mixture heated on a steam bath for twelve hours (temperature of contents of vessel 90°–95° C). The contents of the flask are thereafter poured into a second vessel containing 100 grams sodium acetate dissolved in 250 milliliters water. The organic liquid phase of the mixture is separated from the aqueous phase by steam distillation. Crude aldehyde is thereafter precipitated from aqueous solution and the solids recystalized from acetic acid and from benzene. The solids thus obtained are further extracted in a soxhlet extractor with 30–60 pet ether. The material remaining in the extraction thimble is 3-perylenecarboxaldehyde, mp 230° C; yield 9.5 grams.

EXAMPLE III

Preparation of poly(p-acetylstyrene)

In a 2 liter three necked flask, fitted with a mechanical stirrer, a dropping funnel, and a reflux condenser are placed 67 grams (0.5 moles) aluminum chloride (reagent grade) and 250 ml. carbon disulfide. Thirty grams (0.37 moles) of acetyl chloride is now introduced into the flask with rapid stirring. While maintaining the contents of the flask in a constant state of agitation, a dope comprising 26 grams poly(styrene), (intrinsic viscosity of 1.06 at a concentration of 2.5 grams/liter of chloroform), in 200 ml. carbon disulfide is gradually added over a period of about 20 minutes. Upon the addition of the polymer, the mixture becomes yellow and a fluffy precipitate forms. The contents of the flask are now heated under reflux conditions and hydrogen chloride gas evolved. Upon completion of the addition of the polymer, the mixture is refluxed for an additional 90 minutes until evolution of hydrogen chloride gas ceases. The mixture is maintained in a constant state of agitation during the period of reflux. The reflux condenser is now opened and the vapors emanating from the flask allowed to escape. After about 70 percent of the carbon disulfide has evaporated, the yellow mass remaining in the bottom of the flask is poured into ice water, and acidified with hydrochloric acid. This acidified dispersion is now steamed for removal of residual traces of cadmium sulfide and the acidic fluid separated from the solids by decantation. Polymer solids remaining in the container are now washed with cold water, the polymer solids separated from the wash by filtration an dried. The polymer obtained in the manner described above is only partially acetylated (approximately 90–95 percent) and, thus, contains recurring structural units from both styrene and p-acetylstyrene.

This polymer is then be reacted with one or more of the following aldehyde functional photosensitive compounds.

| | Photosensitive Compounds | Source |
|---|---|---|
| (a) | N-ethyl-carbazole-3-carboxaldehyde | Aldrich Chemical Co., Milwaukee, Wisconsin, Catalogue No. 15,148-3 |
| (b) | pyrene-1-carboxaldehyde | Aldrich Chemical Co., Milwaukee, Wisconsin, Catalogue No. 14,403-7 |
| (c) | 9-anthraldehyde | Aldrich Chemical Co., Milwaukee, Wisconsin, Cata- |

-continued

| | Photosensitive Compounds | Source |
|---|---|---|
| (d) | 1-naphthaldehyde | logue No. 12,323-4 Aldrich Chemical Co., Milwaukee, Wisconsin, Catalogue No. N-10-9 |
| (e) | 2-naphthaldehyde | Aldrich Chemical Co., Milwaukee, Wisconsin, Catalogue No. N-20-6 |
| (f) | julolidine-9-carboxaldehyde | Example I |
| (g) | 3-perylenecarboxaldehyde | Example II |

To a solution of 10 grams poly(p-acetylstyrene) dissolved in a mixture of 190 grams glacial acetic acid and 25 grams photosensitive aldehyde is added 10 grams of a 10 percent (by weight) solution of concentrated sulfuric acid in glacial acetic acid. The mixture is placed in the dark and the contents allowed to for 24 hours. During this interval, the reaction mass is periodically agitated. At the end of this 24-hour interval, anhydrous sodium acetate is added to the mixture to neutralize the sulfuric acid catalyst. The contents of the flask are now poured into 500 milliliters of methanol (95 percent) and the polymeric solids which precipitate, separated from the methanol by filtration and dried in a vacuum of oven 60° C. A 25-weight percent solution of such solids in tetrahydrofuran are draw bar coated on a sheet of NESA glass and the electrophotographic properties of the resultant film evaluated using a Xerox Model D Processor. Image information is projected onto the surface of the (slightly) yellowish film utilizing actinic radiation. The intensity and duration of the exposure is sufficient to selectively discharge the surface charge in those areas of the film subjected to such exposure. The latent image thus produced is rendered visible by development with a carbon black pigment thermoplastic developer composition. The developed image is transferred to a receiving sheet and fused thereto, Developer particles remaining on the surface of the film are removed by wiping with a soft cotton cloth. Developed image quality is satisfactory.

EXAMPLE IV

The procedures of Example III are repeated except for the substitution of poly(methyl-vinylketone) for poly(p-acetylstyrene); methyl vinylketone monomer being obtained from Pfaltz and Bauer, Inc., Flushing, New York — Catalog II M 30460.

EXAMPLE V

The procedures of Example III are repeated except for the substitution of poly(methyl-isopropanolketone) for poly(p-acetylstyrene).

EXAMPLE VI

The procedures of Example I are repeated except for the substitution of poly(vinylpyrene), (prepared according to the teachings of U.S. Pat. No. 3,725,505 — which is hereby incorporated by reference in its entirety), for poly(styrene).

EXAMPLE VII

The procedures of Example III are repeated except for for the addition of five parts by weight dinitrobenzene to the tetrahydrofuran solution of polymer prior to the filming of said solution on the NESA glass plate.

EXAMPLE VIII

The procedures of Example VII are repeated except for the substitution of chloranil for dinitrobenzene.

EXAMPLE IX

The procedures of Example VII are repeated except for the substitution of 2,4,7-trinitro-9-fluorenone for dinitrobenzene.

Due to the presence of a chalcone type linkage between the photosensitive moiety ($A_r$) and the polymer backbone, the photoconductive polymers of this invention are capable of undergoing some cross-linking upon aging. In order to accelerate this aging process, films of these polymers can be subjected to exposure to ultraviolet light for a period of anywhere from several minutes to several hours (depending upon the intensity of the light source, its wavelength and position relative to the film). This controlled aging stabilizes the photoresponse of the film and, thus, permits more accurate correlation of imaging process conditions.

What is claimed is:

1. A polymeric composition having recurring structural units of the formula

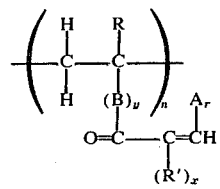

wherein
R is hydrogen or alkyl of 1–4 carbon atoms;
R' is alkyl of 1–4 carbon atoms, cycloalkyl, phenyl, or alkyl substituted phenyl;
B is phenylene or a diradical of a fused aromatic nucleus having up to four benzene rings;
$A_r$ is selected from the group consisting of naphthalene, anthracene, pyrene, perylene, julolidine, carbazole and their respective homologues;
x is 0 or 1;
y is 0 or 1; and
n is at least 2.

2. A polymeric composition comprising a block copolymer having nonphotoconductive segments and photoconductive segments having recurring structural units of the formula:

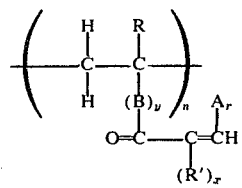

wherein
R is hydrogen or alkyl of 1–4 carbon atoms;
R is alkyl of 1–4 carbon atoms, cycloalkyl, phenyl, or alkyl substituted phenyl;
B is phenylene or a diradical of a fused aromatic nucleus having up to four benzene rings;
$A_r$ is selected from the group consisting of naphthalene, anthracene, pyrene, perylene, julolidine, carbazole and their respective homologues;

x is 0 or 1;
y is 0 or 1; and
n is at least 2.

3. A polymeric composition comprising a preformed nonphotoconductive polymer backbone and polymeric grafts appended therefrom which have recurring structural units of the formula:

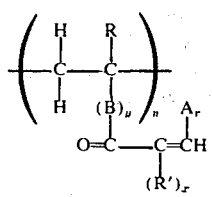

wherein
R is hydrogen or alkyl of 1–4 carbon atoms;
R' is alkyl of 1–4 carbon atoms, cycloalkyl, phenyl, or alkyl substituted phenyl;
B is phenylene or a diradical of a fused aromatic nucleus having up to four benzene rings;
$A_r$ is selected from the group consisting of naphthalene, anthracene, pyrene, perylene, julolidine, carbazole and their respective homologues;
x is 0 or 1;
y is 0 or 1; and
n is at least 2.

4. A polymeric composition having recurring structural units of the formula:

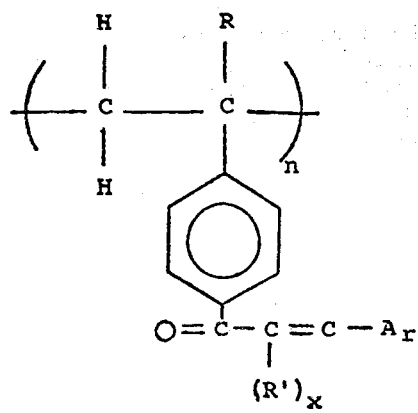

wherein
R is hydrogen or alkyl of 1–4 carbon atoms;
R' is alkyl of 1–4 carbon atoms, cycloalkyl, phenyl, or alkyl substituted phenyl;
$A_r$ is selected from the group consisting of naphthalene, anthracene, pyrene, perylene, julolidine, carbazole and their respective homologues;
x is 0 or 1; and
n is at least 2.

5. A polymeric composition comprising a block copolymer having nonphotoconductive segments and photoconductive segments having recurring structural units of the formula:

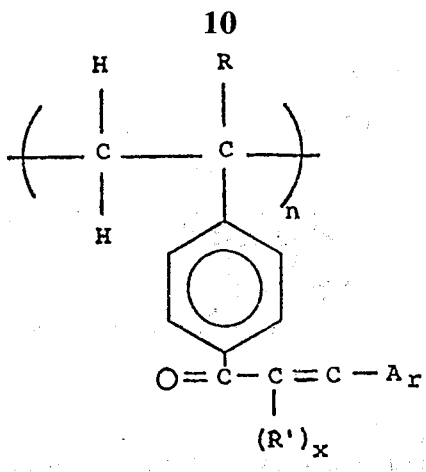

wherein
R is hydrogen or alkyl of 1–4 carbon atoms;
R' is alkyl of 1–4 carbon atoms, cycloalkyl, phenyl, or alkyl substituted phenyl;
$A_r$ is selected from the group consisting of naphthalene, anthracene, pyrene, perylene, julolidine, carbazole and their respective homologues;
x is 0 or 1; and
n is at least 2.

6. A polymeric composition comprising a preformed nonphotoconductive polymer backbone and polymeric graft appended therefrom which have recurring structural units of the formula:

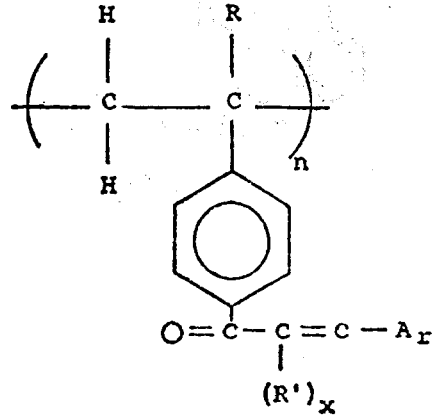

wherein
R is hydrogen or alkyl of 1–4 carbon atoms;
R' is alkyl of 1–4 carbon atoms, cycloalkyl, phenyl, or alkyl substituted phenyl;
$A_r$ is selected from the group consisting of naphthalene, anthracene, pyrene, perylene, julolidine, carbazole and their respective homologues;
x is 0 or 1; and
n is at least 2.

7. A polymeric composition having recurring structural units of the formula:

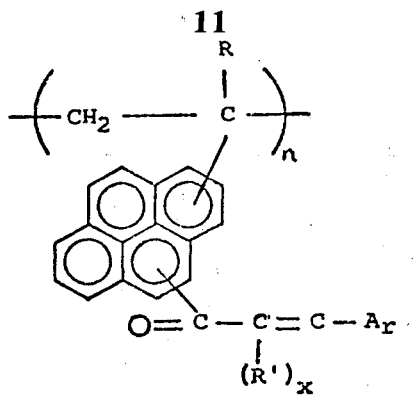

wherein
R is hydrogen or alkyl of 1–4 carbon atoms;
R' is alkyl of 1–4 carbon atoms, cycloalkyl, phenyl, or alkyl substituted phenyl;
$A_r$ is selected from the group consisting of naphthalene, anthracene, pyrene, perylene, julolidine, carbazole and their respective homologues;
$x$ is 0 or 1; and
$n$ is at least 2.

8. A polymeric composition comprising a block copolymer having nonphotoconductive segments and photoconductive segments having recurring structural units of the formula:

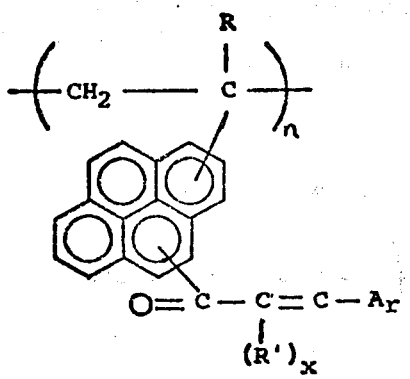

wherein
R is hydrogen or alkyl of 1–4 carbon atoms;
R' is alkyl of 1–4 carbon atoms, cycloalkyl, phenyl, or alkyl substituted phenyl;
$A_r$ is selected from the group consisting of naphthalene, anthracene, pyrene, perylene, julolidine, carbazole and their respective homologues;
$x$ is 0 or 1; and
$n$ is at least 2.

9. A polymeric composition comprising a preformed nonphotoconductive polymer backbone and polymeric graft appended therefrom which have recurring structural units of the formula:

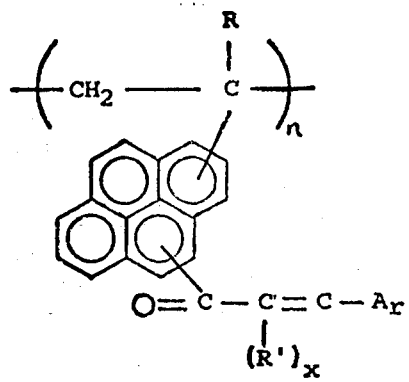

wherein
R is hydrogen or alkyl of 1–4 carbon atoms;
R' is alkyl of 1–4 carbon atoms, cycloalkyl, phenyl, or alkyl substituted phenyl;
$A_r$ is selected from the group consisting of naphthalene, anthracene, pyrene, perylene, julolidine, carbazole and their respective homologues;
$x$ is 0 or 1; and
$n$ is at least 2.

* * * * *